United States Patent [19]

Williams

[11] Patent Number: 5,415,624

[45] Date of Patent: May 16, 1995

[54] THERAPEUTIC BRACE WITH ALTERNATIVE INSERTABLE AND REMOVABLE HOT AND COLD PODS

[75] Inventor: Steve Williams, Chicago, Ill.

[73] Assignee: World Class Technologies, Inc., Chicago, Ill.

[21] Appl. No.: 126,793

[22] Filed: Sep. 24, 1993

[51] Int. Cl.⁶ .............................. A61F 5/01; A61F 7/00
[52] U.S. Cl. .......................................... 602/21; 602/14; 602/61; 602/2; 607/111; 607/114
[58] Field of Search ......................... 602/21, 20, 14, 64, 602/2, 21; 607/106, 109, 111, 112, 114; 473/62; 273/166 R, 169 R, 169 A

[56] References Cited

U.S. PATENT DOCUMENTS

| | | |
|---|---|---|
| 3,327,703 | 8/1964 | Gamm . |
| 4,077,390 | 3/1978 | Stanley et al. . |
| 4,527,566 | 7/1985 | Abare ................................. 607/112 |
| 4,556,055 | 12/1985 | Bonner, Jr. ....................... 602/2 X |
| 4,572,158 | 2/1986 | Fiedler . |
| 4,625,729 | 12/1986 | Roney ................................ 607/108 |
| 4,880,953 | 11/1989 | Manker . |
| 4,972,832 | 11/1990 | Tradini et al. ..................... 602/2 X |
| 5,000,176 | 3/1991 | Daniel ............................... 607/108 |
| 5,014,689 | 5/1991 | Meunchen et al. . |
| 5,165,402 | 11/1992 | McCoy .............................. 607/108 |
| 5,295,949 | 3/1994 | Hathaway ......................... 602/14 X |

OTHER PUBLICATIONS

*Business Day, The New York Times,* Jun. 7, 1993, "Patents/With a technique similar to baloon angioplasty, a doctor tackles carpal tunnel syndrome" by Sabra Chartrand.

"The Handling of an Epidemic—Repetitive Stress Injury"—Feb. 19, 1993 *Working Woman,* pp. 60–65 by David Heilbroner.

*The Wall Street Journal: Enterprise,* Aug. 24, 1992 "Innovations for Carpal-Tunnel Syndrome Prospering" by Paul J. Lim.

*The Time Herald Record* reprint from Chicago Tribune of "Carpal Tunnel Syndrome" by Rick Tuma (undated).

Primary Examiner—Richard J. Apley
Assistant Examiner—Beverly A. Meindl
Attorney, Agent, or Firm—Leydig, Voit & Mayer, Ltd.

[57] ABSTRACT

A wearable therapeutic brace having strategically located pockets that receive and contain reusable, alternatively insertable hot and cold pods which can be tailored to a specific injury management program of use. The brace body portion which may be a hand/wrist, neck/cervical collar, knee/elbow/ankle brace has a main section of elasticized material construction with adjustable fastening means and fitted pockets formed from breathable, four way stretch nylon (LYCRA) spandex for receiving the hot or cold gel filled reusable pods to be held adjacent the appropriate body part area.

15 Claims, 5 Drawing Sheets

THERAPEUTIC BRACE WITH ALTERNATIVE INSERTABLE AND REMOVABLE HOT AND COLD PODS

BACKGROUND OF THE INVENTION

The present invention relates generally to therapeutic support braces, and, more particularly, relates to an improved construction and arrangement of wearable braces to provide treatment of and relief from repetitive stress injury (RSI) in various parts of the body. More specifically, though not so limited, the brace of this invention is directed to relief from carpal tunnel syndrome resulting from continuous wrist and hand motions. The preliminary forms of such braces were disclosed in Disclosure Document No. 318,356, filed in the United States Patent and Trademark Office on Oct. 1, 1992 and Disclosure Document No. 318,663, filed in the U.S. Patent and Trademark Office on Oct. 1, 1992 for "Wrist Brace" and "Knee Brace", respectively.

DESCRIPTION OF THE PRIOR ART

Repetitive stress injury (RSI) is becoming more and more common and troublesome both in the work place and in leisure or sporting activities. The costs associated with RSI have already reached staggering proportions as currently reported. (See *Business Day, The New York Times,* Monday, Jun. 7, 1993, "Patents/With A Technique Similar To Balloon Angioplasty, Doctors Tackle Carpal Tunnel Syndrome" which reports on a surgical procedure patent, U.S. Pat. No. 5,179,963; "The Handling of an Epidemic—Repetitive Stress Injury," Feb. 19, 1993 *Working Woman,* pages 60–65; *The Wall Street Journal:* Enterprise, Aug. 24, 1992 "Innovations for Carpal-Tunnel Syndrome Prospering".)

Among the most serious of the repetitive stress injuries is carpal tunnel syndrome which results from continuous wrist and hand motions which can cause a ligament to thicken and press on the nerves and tendons running through the carpal tunnel, a cluster of bones in the wrist and palm. Other such problems which have been occurring and coming under the category of RSI are tenosynovitis and myofascitis, or inflammation of the tendons, connective tissues and muscles, and de Quervain's disease, a tendinitis of the thumb which similarly arises from continuous and repetitive thumb actions required to be performed in the same manual task. The patent art is replete with support braces to control or reduce cumulative traumas to the wrist from carpal tunnel syndrome, e.g. U.S. Pat. No. 3,327,703 and 5,014,689. While such elastic support braces alone do provide necessary physical support to alleviate discomforts brought about by the RSI injury, they do not provide either a means of treating or preventing the major chronic conditions associated with RSI, such as the stiffness due to lock up of ligaments and joints, inflammation of the tendons, connective tissues and muscles, and weakness due to the pain, inflammation and numbness. At best, such existing devices merely approach the problem from the standpoint of restriction of certain movements and support.

OBJECTS AND SUMMARY OF THE INVENTION

Accordingly, it is a primary objective of this invention to provide improved brace arrangements, particularly constructed to address or manage the problems of pain, inflammation and stiffness as well as providing support or restriction of motion for controlling or alleviating cumulative trauma from RSI in various body parts. In particular, and while not so limited, it is an object of the present invention to provide an improved hand/wrist brace which can be worn as a conventional brace but also provides means for aiding in the reduction of swelling and dilation of inflamed body parts as well as to provide alternative relief for the rehabilitation and prevention of carpal tunnel syndrome symptoms.

In general, the present invention contemplates a wearable brace having strategically located pockets that receive and contain reusable, alternatively insertable hot and cold pods which can be tailored to a specific injury management program of use. The brace includes a typical elasticized material body portion construction with adjustable fastening means for affixing the brace and the fitted pockets are positioned to accommodate the selective insertion of either hot or cold gel filled reusable pods adjacent the appropriate body part areas. The pockets are formed from breathable, comfortable material attached to the body portion that enables the transmission of either heat or cold from the pods to the adjacent body part areas. Preferably the pocket material is a four-way stretch nylon (LYCRA) spandex or the like material. The pods which may be specially shaped for conformance and comfort comprise edge sealed vinyl pouches that contain liquid, or gel that may include glycerine or sodium acetate in water compositions which are either heatable by boiling or in a microwave, or may be frozen in a freezer. The brace may also include appropriate stiffeners or stays insertable in pockets provided on the outside brace body portion surface such as under-the-palm splint or volar stay provided with the wrist/hand brace.

These and other features and advantages of the invention will be more readily apparent upon reading the following description of a preferred exemplified embodiment of the invention and upon reference to the accompanying drawings wherein:

BRIEF DESCRIPTION OF THE DRAWINGS

FIG. 4A is a top plan view of a stiffener for use with hand brace;

FIG. 4B is a side view of the stiffener of FIG. 4A;

DETAILED DESCRIPTION OF THE INVENTION

Figure 1:
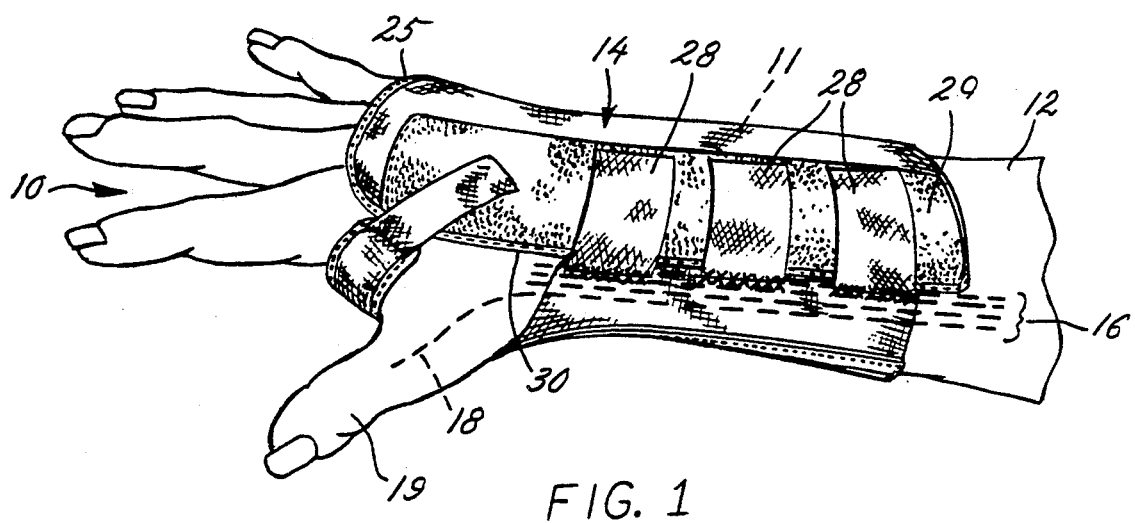
FIG. 1 is a perspective view illustrating an exemplary hand brace in accordance with the principles of this invention on a user's hand.
Figure 2:
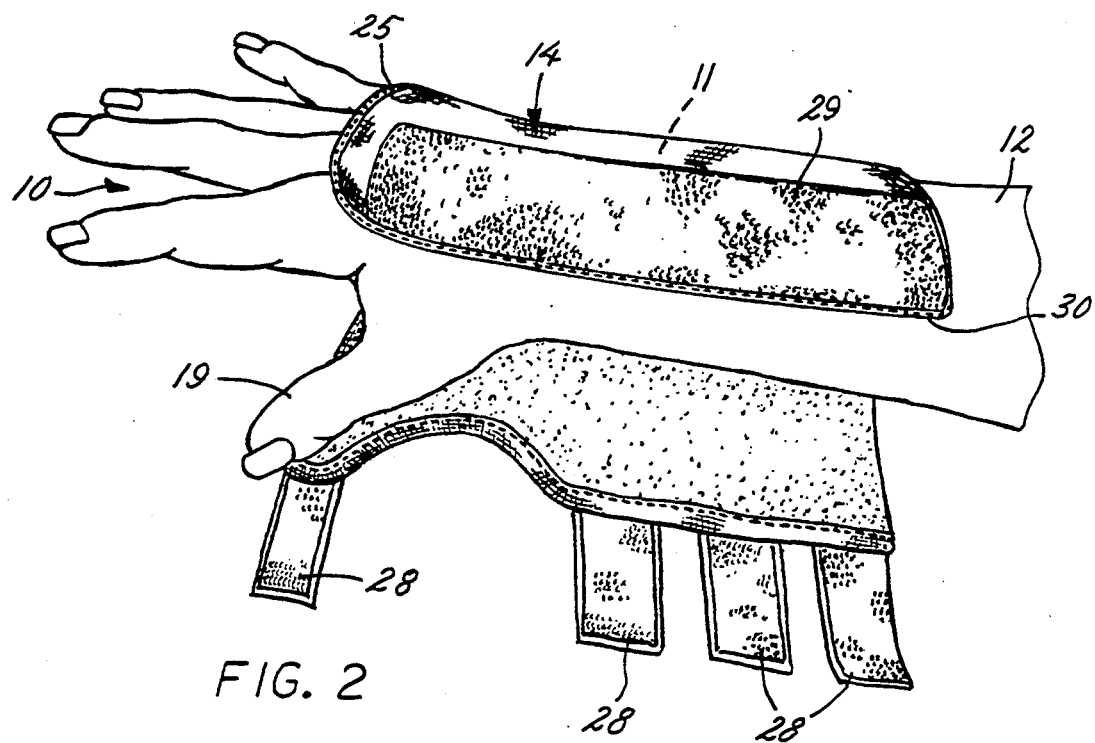
FIG. 2 is a perspective view similar to FIG. 1, illustrating an initial step in installation of the exemplary hand brace.
Figure 3:
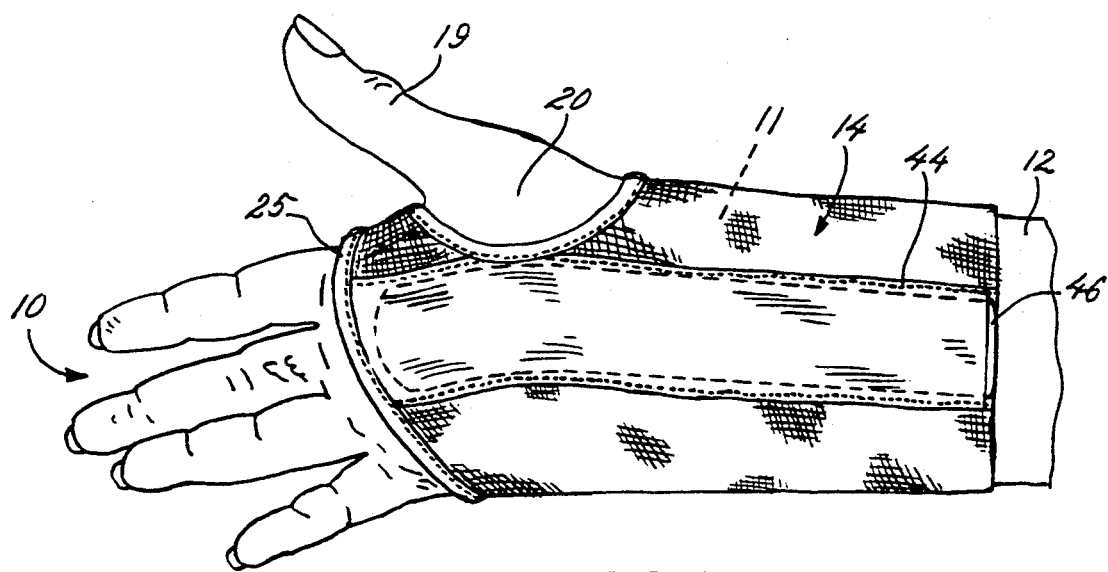
FIG. 3 is a perspective view illustrating the inner side of the installed hand brace on a user's hand.

Turning to the drawings, there is shown in FIGS. 1 through 3, the installation of the exemplary hand brace to a user's hand with the brace containing one of the sets of alternative hot/cold pods within its interior pockets. It should be understood, however, as the discussion proceeds that with respect to the present invention, insofar as it provides an injury management system for RSI types of problems, the brace could likewise be provided in the form of cervical collar for neck sprains and injuries, or knee, elbow or ankle braces for respective injuries to those body part areas.

Figure 4:
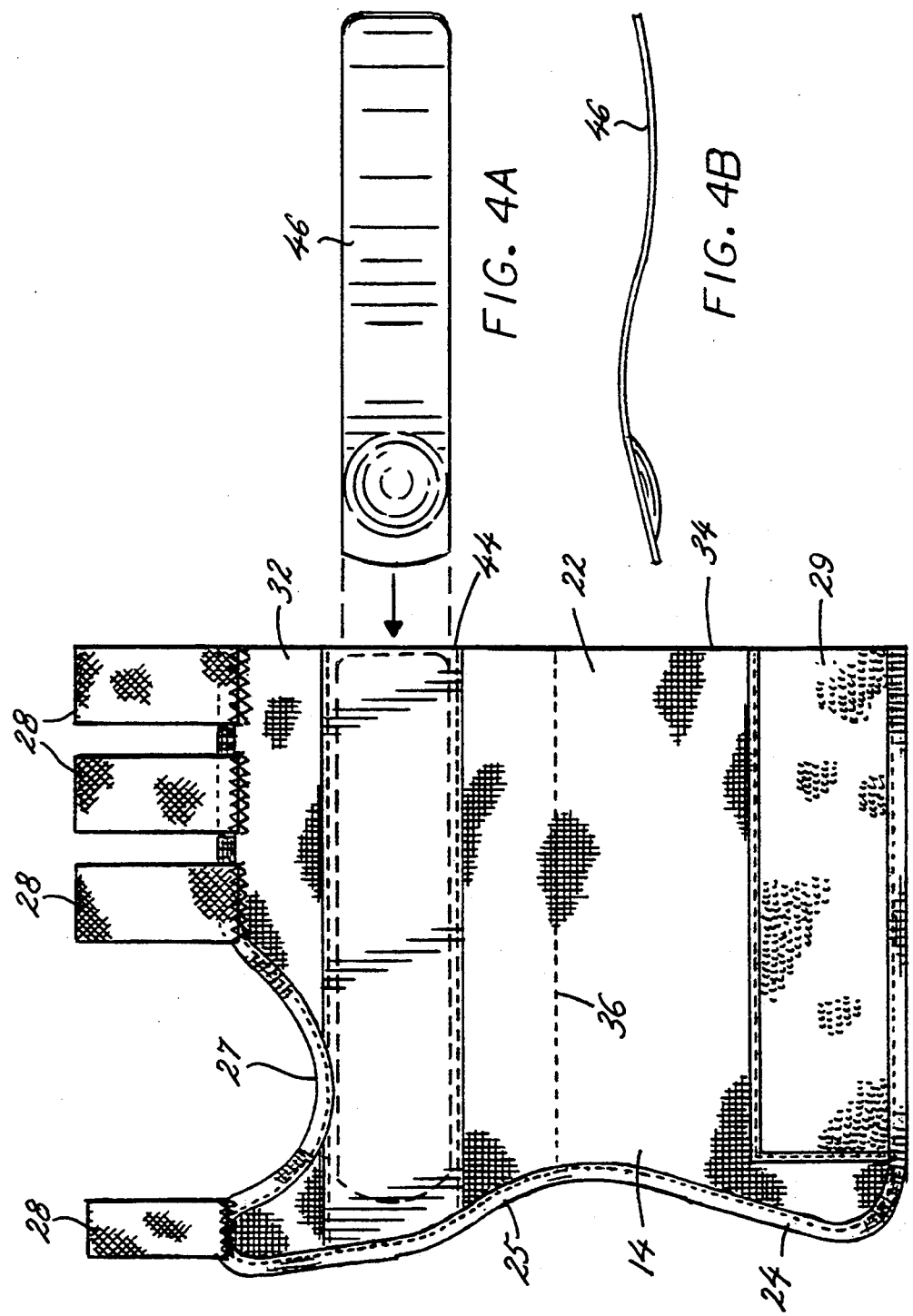
FIG. 4 is a top plan view of the outside of the exemplary hand brace in accordance with the principles of this invention.

As illustrated in FIGS. 1-3, the right hand, generally indicated at 10, including wrist 11 and arm portion 12 receives a hand brace 14. As illustrated diagrammatically in these figures, the carpal ligaments run generally beneath the wrist 11, indicated at 16, with the carpal tunnel being defined by those carpal ligaments. The hand 10 also includes transcarpal ligaments as shown at 18 which connect with the thumb 19. The transcarpal ligaments are relevant to the thenar area or ball 20 of the thumb 19. Carpal tunnel syndrome results from injury by way of strain or sprain to the carpal ligaments of the wrist. The de Quervain's condition results from injury or strain or sprain of the transcarpal ligaments. In either event, such injuries typically involve swelling or inflammation of the tendon sheets and persons so afflicted may experience tingling or numbness in their hands or even feel a burning pain in the arm. The hand brace 14 of this invention, as illustrated with reference to FIG. 4, includes essentially a four sided body portion or strip of material 22 stretchable in all directions. Preferably this material is an elastic fabric stretchable at least in two directions. The edges may be finished with a binding 24 also of a stretchable material, particularly in the horizontal directions as depicted in FIG. 4. The upper edge 25 includes a contour to conform with the hand 10 when wrapped around with the edge 26 at the left as viewed in FIG. 4 including an indentation 27 which fits around the thumb 19 and particularly the thenar area thereof. Provided at locations along the edge 26 are outwardly projecting strips 28 of looped portions of hook and loop type of fasteners, such as the velcro type fastener and the strip of the hook portion 29 of such fasteners is provided along the opposite edge 30 on the external side of the brace.

Figure 5:
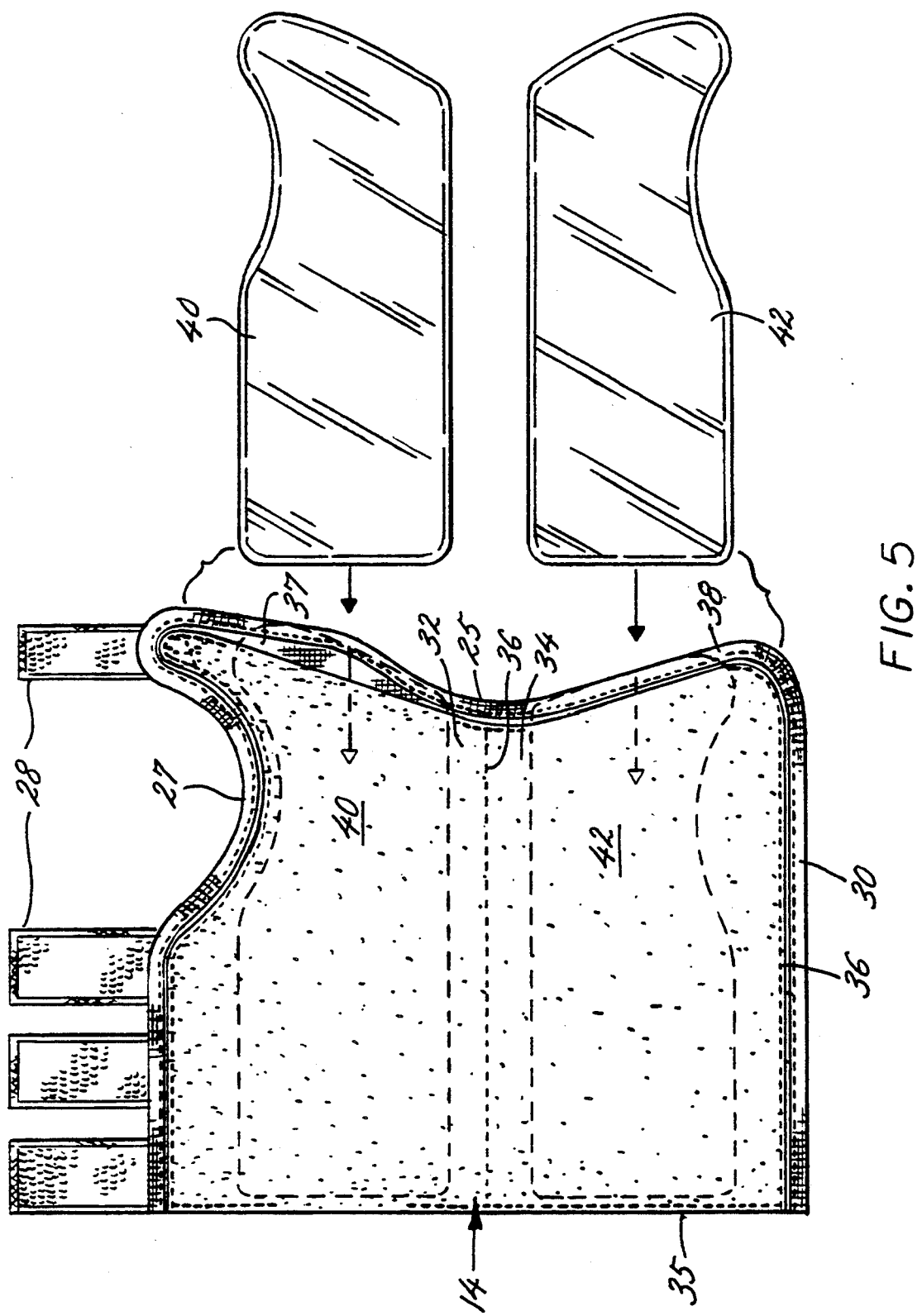
FIG. 5 is a view similar to FIG. 4, but here illustrating the inside of the brace and with the alternatively insertable hot/cold pods in the pockets of the present brace and exploded outside therefrom.
Figure 6:
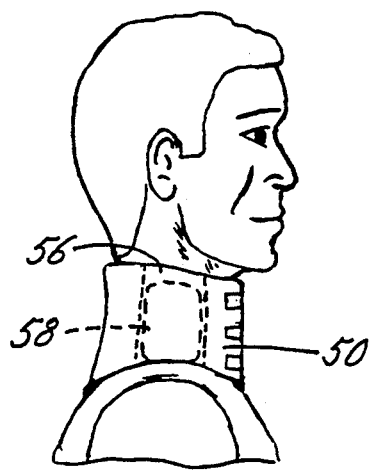
FIG. 6 is a perspective view of an alternative brace employing the principles of the present invention here illustrated as a neck or cervical collar.
Figure 7:
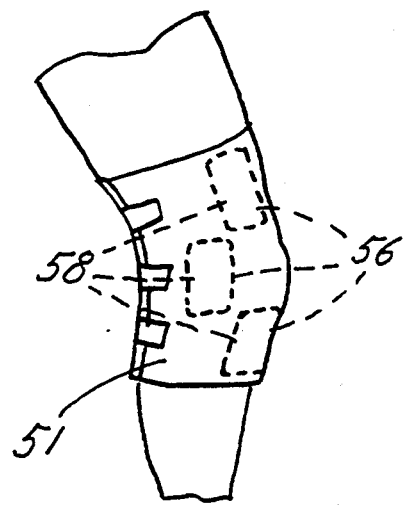
FIG. 7 is a perspective view of another alternative brace here illustrated as a knee brace.
Figure 8:
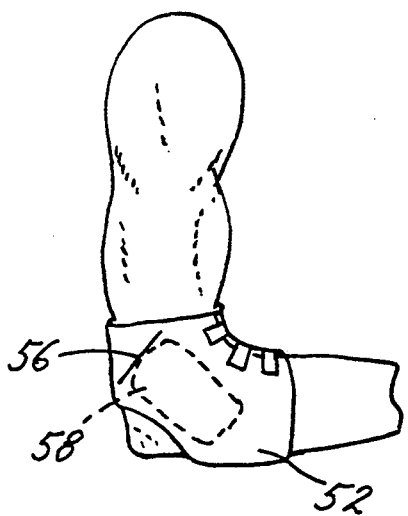
FIG. 8 is a perspective view of yet another brace here illustrated as an elbow brace.
Figure 9:
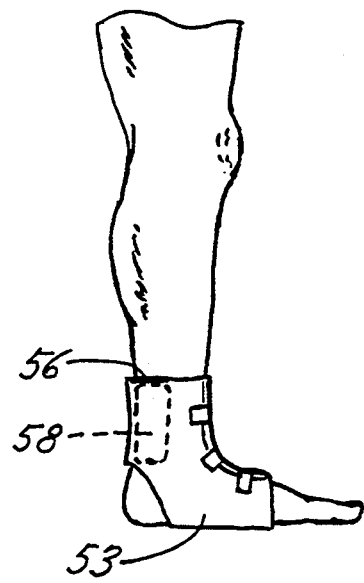
FIG. 9 is a perspective view of still another brace here illustrated as an ankle brace.

In accordance with the present invention, referring to FIG. 5, on the internal side of the brace there is here provided a pair of pockets 32, 34, defined by breathable material such as four way stretch nylon (LYCRA) spandex which is sewed about the periphery sides 26, 30, and bottom 35 as well as down across the middle as seen by sew line 36. Openings 37, 38 at the upper end edge 25 allow for insertion of liquid containing pods 40, 42. The pods are pouch like with edges sealed all around and contain a liquid such as glycerin or sodium acetate in water composition appropriately selected for either reusable heating in boiling water or in a microwave or cooling by freezing. Preferably two sets of pods are provided, one for heating and one for application of cold along with the brace. The cold liquid pods may be provided with a blue coloring while the hot pods would be provided with a red coloring to have suitable indicia for clearly pointing out their respective purposes. The pockets 32 and 34 on the inner side of the elastic brace are positioned so that one pod 40 inserted therein is positioned under the wrist 11 while the other pod 42 is positioned on top of the wrist 11.

With the present arrangement and the selective choice of either heated or frozen pods, the user can select a routine for better and more effective management of the RSI or control of the same. The heated pods would be applied to deal with stiffness that may come about such as from sleep inactivity. The frozen pods can be applied when needed, to slow and manage the daily build up of inflammations from repetitive motion activities. The routine might be employed during the course of the day where heat would be applied in the morning, work performed with the brace alone followed by some break session where frozen pods may be applied, followed by wearing the brace alone and then followed again by frozen pods to control inflammation and after which the heated pods are used to relieve stiffness.

At the under side of the brace (FIG. 4), adjacent the palmar area, is a pocket 44 which receives a removable volar stay or stiffener 46 (FIGS. 4A & 4B) that acts as a splint and support for the thenar area of the thumb. Other stays or supports may be provided depending on the type of brace or restriction of movement that may be prescribed.

Referring to FIGS. 7-10, respectively, there is shown illustrative examples of the application of the principles of the present invention to braces 50-53 for the neck, knee, elbow and ankle of a person with pockets 56 holding hot/cold pods 58 for appropriate injury management.

I claim as my invention:

1. A therapeutic brace for providing support and treatment to an anatomical part subject to repetitive stress injuries before, during, and after repetitive activity comprising:
    a main section made up of breathable elastic material, said main section being contoured to the anatomical part and adapted to be wrapped around the anatomical part, said main section including releasable fastening means to hold the main section in the wrapped position, the internal side of said main section having at least one pocket positioned adjacent to injury susceptible areas of the anatomical part which said main section overlies, and a liquid containing pod receivable in said pocket, the pod being contoured to the shape of the anatomical part and being adaptable to either heating or freezing for the selective application of heat or cold to the anatomical part, said main section having at least two separate pockets
    whereby said main section provides properly distributed support to the anatomical part, and said pod provides properly distributed thermal treatment to the anatomical part.

2. A therapeutic brace as claimed in claim 1 wherein each of said pockets receives separate liquid containing pods, each of said pods being contoured to the anatomy of the anatomical part.

3. A therapeutic brace as claimed in claim 2 which includes a splint stiffener and a receiving pocket for the splint stiffener on the main section.

4. A therapeutic brace as claimed in claim 1 wherein said main section is contoured for use on a hand and said pocket is for holding a pod specially contoured for the hand and overlying the wrist.

5. A therapeutic brace as claimed in claim 1 wherein said main section is contoured for use on a knee and said pocket is for holding a pod specially contoured for the knee and adjacent the kneecap.

6. A therapeutic brace as claimed in claim 1 wherein said main section is contoured for use on an elbow and said pocket is for holding a pod specially contoured for the elbow and adjacent the elbow joint.

7. A therapeutic brace for providing support and treatment to an anatomical part subject to repetitive stress injuries before, during, and after repetitive activity comprising:

a main section made up of breathable elastic material, said main section being contoured to the anatomical part and adapted to be wrapped around the anatomical part, said main section including releasable fastening means to hold the main section in the wrapped position, the internal side of said main section having at least one pocket positioned adjacent to injury susceptible areas of the anatomical part which said main section overlies, and a liquid containing pod receivable in said pocket, the pod being contoured to the shape of the anatomical part and being adaptable to either heating or freezing for the selective application of heat or cold to the anatomical part wherein separate pods include a red colored liquid for indicia of heating and a blue colored liquid for indicia of cooling;

whereby said main section provides properly distributed support to the anatomical part, and said pod provides properly distributed thermal treatment to the anatomical part.

8. A therapeutic brace for providing support and treatment to an anatomical part subject to repetitive stress injuries before, during, and after repetitive activity comprising:

a main section made up of breathable elastic material, said main section being contoured to the anatomical part and adapted to be wrapped around the anatomical part, said main section including releasable fastening means to hold the main section in the wrapped position, the internal side of said main section having at least one pocket positioned adjacent to injury susceptible areas of the anatomical part which said main section overlies, and a liquid containing pod receivable in said pocket, the pod being contoured to the shape of the anatomical part and being adaptable to either heating or freezing for the selective application of heat or cold to the anatomical part, said main section pocket including an outward side made of four way stretch nylon spandex;

whereby said main section provides properly distributed support to the anatomical part, and said pod provides properly distributed thermal treatment to the anatomical part.

9. A therapeutic brace as claimed in claim 8 wherein said main section is contoured for use on an ankle and said pocket is for holding a pod specially contoured for the ankle and adjacent to the ankle region.

10. A therapeutic brace for providing support and treatment to the wrist before, during, and after repetitive activity leading to repetitive stress injuries comprising:

a main section made up of breathable elastic material adapted to be wrapped around the wrist, lower arm and portions of the hand including the palmar portion and contoured to provide properly distributed support to the wrist lower arm and hand, said main section including releasable fastening means to hold the main section in the wrapped position, the internal side of said main section having at least one pocket positioned adjacent to injury susceptible areas of the wrist which said main section overlies, and a liquid containing pod receivable in said pocket, the pod being contoured to the anatomy of the wrist, lower arm and portions of the hand including the palmar portion and being adaptable to either heating or freezing for the selective application of heat or cold to the wrist lower arm and hand.

11. A therapeutic brace as claimed in claim 10 having at least two separate pockets on said main section.

12. A therapeutic brace as claimed in claim 11 wherein each of said pockets receives separate liquid containing pods, each of said pods being contoured to the anatomy of the wrist and hand.

13. A therapeutic brace as claimed in claim 10 which includes a splint stiffener and a receiving pocket for the splint stiffener on the main section.

14. A therapeutic brace as claimed in claim 10 wherein said main section pocket includes an outward side made of four way stretch nylon spandex.

15. A therapeutic brace as claimed in claim 10 wherein separate pods include a red colored liquid for indicia of heating and a blue colored liquid for indicia of cooling.

* * * * *